United States Patent
Shamdasani et al.

(10) Patent No.: US 10,729,404 B2
(45) Date of Patent: Aug. 4, 2020

(54) ULTRASOUND SYSTEM AND METHOD FOR MEASUREMENT USING SHEAR WAVE

(71) Applicant: KONINKLIJKE PHILIPS N.V., Eindhoven (NL)

(72) Inventors: Vijay Thakur Shamdasani, Eindhoven (NL); Yin Hui Deng, Eindhoven (NL); Ying Wu, Eindhoven (NL); Hua Xie, Cambridge, MA (US); Shiwei Zhou, Acton, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 332 days.

(21) Appl. No.: 15/515,392

(22) PCT Filed: Jul. 29, 2016

(86) PCT No.: PCT/EP2016/068250
§ 371 (c)(1),
(2) Date: Mar. 29, 2017

(87) PCT Pub. No.: WO2017/021341
PCT Pub. Date: Feb. 9, 2017

(65) Prior Publication Data
US 2018/0228463 A1    Aug. 16, 2018

(30) Foreign Application Priority Data

Aug. 3, 2015  (WO) ............... PCT/CN2015/085935
Sep. 25, 2015  (EP) ..................................... 15186920

(51) Int. Cl.
  *A61B 8/08*   (2006.01)
  *G01S 7/52*   (2006.01)
  *G01S 15/89*   (2006.01)

(52) U.S. Cl.
  CPC .............. *A61B 8/085* (2013.01); *A61B 8/485* (2013.01); *A61B 8/5223* (2013.01);
  (Continued)

(58) Field of Classification Search
  CPC ....... A61B 8/085; A61B 8/5223; A61B 8/485; G01S 15/8927; G01S 7/5208; G01S 7/52042; G01S 7/52095; G01S 7/52022
  See application file for complete search history.

(56) References Cited

U.S. PATENT DOCUMENTS 8,343,050 B2   1/2013  Fan et al.
8,494,791 B2 * 7/2013  Hazard .................. A61B 8/485
                                                            382/131

(Continued)

FOREIGN PATENT DOCUMENTS

WO   2014055410 A1   4/2014
WO   2014055973 A1   4/2014
WO   WO-2015114232 A1 *  8/2015 ............. A61B 8/485

*Primary Examiner* — Boniface N Nganga (57) ABSTRACT

The present invention proposes an ultrasound imaging system and method for measuring a property of a region of interest in a subject by using shear wave, wherein an ultrasound probe is configured to sequentially transmit, to each of a plurality of focal spots (320, 322, 324) in the region of interest, a push pulse (310, 312, 314) for generating a shear wave (330, 332, 334), each of the plurality of focal spots having a mutually different depth value ($z_1$, $z_2$, $z_3$), and to receive ultrasound echo signals adjacent (350, 352, 354) to each of the plurality of focal spots; a shear wave detector is configured to derive, for each of the plurality of focal spots, a first parameter indicating a property of the generated shear wave, based on the received ultrasound echo signals; and a property estimator is configured to estimate a second parameter indicating the property of the region of interest as a function of the derived first parameters.

15 Claims, 5 Drawing Sheets

(52) U.S. Cl.
CPC ........ *G01S 7/5208* (2013.01); *G01S 7/52022* (2013.01); *G01S 7/52042* (2013.01); *G01S 7/52095* (2013.01); *G01S 15/8927* (2013.01)

(56) References Cited

U.S. PATENT DOCUMENTS

| | | | |
|---|---|---|---|
| 8,500,639 B2 | 8/2013 | Yao | |
| 8,602,994 B2 | 12/2013 | Zheng et al. | |
| 8,734,350 B2 | 5/2014 | Greenleaf et al. | |
| 8,734,352 B2 | 5/2014 | Burgher et al. | |
| 8,758,248 B2 | 6/2014 | Lin et al. | |
| 2009/0056453 A1* | 3/2009 | McAleavey | A61B 8/08 73/597 |
| 2011/0184287 A1* | 7/2011 | McAleavey | A61B 8/4483 600/438 |
| 2011/0263978 A1* | 10/2011 | Chen | A61B 8/48 600/438 |
| 2012/0089019 A1* | 4/2012 | Fan | A61B 8/485 600/437 |
| 2012/0226158 A1* | 9/2012 | Greenleaf | A61B 6/5217 600/438 |
| 2013/0123630 A1 | 5/2013 | Frieburger et al. | |
| 2013/0131511 A1* | 5/2013 | Peterson | A61B 5/0048 600/438 |
| 2013/0289402 A1* | 10/2013 | Tabaru | A61B 8/08 600/438 |
| 2013/0345565 A1 | 12/2013 | Fan et al. | |
| 2014/0005548 A1 | 1/2014 | Fraser et al. | |
| 2014/0018679 A1 | 1/2014 | Chen et al. | |
| 2014/0046173 A1 | 2/2014 | Greenleaf et al. | |
| 2014/0276058 A1 | 9/2014 | Fan et al. | |
| 2016/0345938 A1* | 12/2016 | Tanter | A61B 8/085 |

\* cited by examiner

FIG. 1

PRIOR ART

ULTRASOUND SYSTEM AND METHOD FOR MEASUREMENT USING SHEAR WAVE

This application is the U.S. National Phase application under 35 U.S.C. § 371 of International Application No. PCT/EP2016/068250, filed on Jul. 29, 2016, which claims the benefit of CN Application Serial No. PCT/CN2015/0859353, filed Aug. 3, 2015 and EP 15186920.3 filed Sep. 25, 2015. These applications are hereby incorporated by reference herein.

FIELD OF THE INVENTION

The present invention relates to an ultrasound system and method for measurement using shear wave, particularly to measuring a property of a region of interest in a subject by using shear wave.

BACKGROUND OF THE INVENTION

Mechanical changes in living tissue correlate with pathological changes. For example, tissue viscosity, tissue stiffness (also known as elasticity) and tissue attenuation coefficients (including tissue longitudinal-wave attenuation, and tissue transverse-wave attenuation, which is also known as shear wave attenuation) are important physical parameters for clinical practice. Various means of remotely interrogating tissue mechanical properties have been developed that exploit the radiation force of an ultrasonic beam to apply force remotely to a region of tissue within the body of a subject such as a patient (acoustic radiation force, also referred to as a push pulse or push beam) to cause deformation of the tissue. Acoustic radiation force can be applied in such a way that elastic properties may be measured, either locally at the point (called focal point) of the deformation by tracking the deformation directly through the use of longitudinal-wave-based ultrasound imaging to follow the pattern of deformation, or at an adjacent region of the focal point by tracking a shear wave propagating laterally away from the deformed region (i.e. the focal point) through shear wave velocity imaging.

Interrogation by ultrasound, for purposes of medical imaging, often makes use of longitudinal waves. A longitudinal wave is characterized by back and forth movement in the direction of propagation. In the conventional tissue attenuation measurement based on a longitudinal wave, the tissue longitudinal-wave attenuation (also called tissue longitudinal attenuation) is estimated based on an ultrasound echo signal which is simultaneously impacted by both the backscatter and attenuation of tissue. Such conventional tissue longitudinal-wave attenuation measurement has the disadvantage that, since it is difficult to separate the impact of the backscatter from that of the tissue attenuation, the accuracy is limited.

Figure 1:
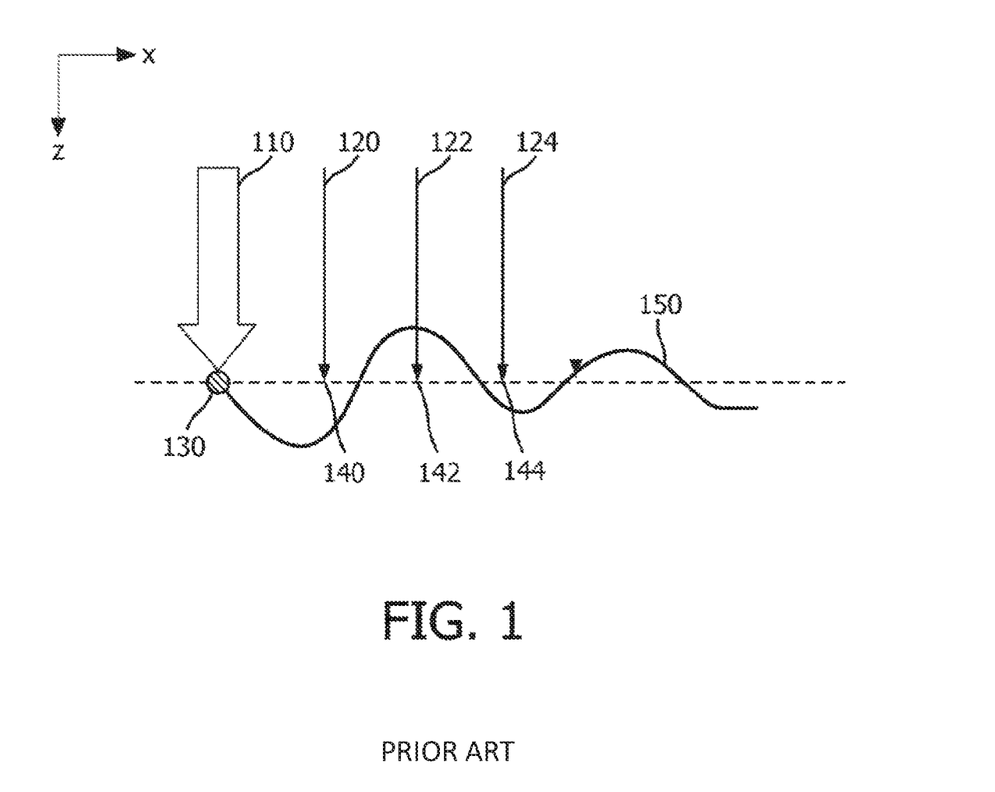
FIG. 1 illustrates a conventional shear wave-based tissue viscosity or elasticity measurement in the prior art.

An ultrasound shear (or transverse) wave, by contrast, is characterized by back and forth movement that is perpendicular to the direction of propagation. Nowadays, many commercial ultrasound scanners offer ultrasound shear wave elastography products to measure tissue shear elasticity. Tissue shear viscosity and shear wave attenuation estimation by means of shear wave elastography have not been commercialized yet. They remain scientifically active research topics as their clinical potential is emerging in certain applications. FIG. 1 illustrates measurement using shear wave according to the prior art. A push pulse (also known as push beam) 110 is transmitted toward a focal spot 130 to generate a shear wave 150 which propagates out from the focal spot in a direction, such as a lateral direction x, perpendicular to the propagation direction of the push pulse (i.e. the longitudinal direction z). One or more tracking pulses (also known as tracking beam) are transmitted, and ultrasound echo signals are received along a plurality of tracking lines (called "A-lines") 120, 122, 124 so as to estimate, at each of a plurality of sampling locations 140, 142, 144 spaced along the lateral direction, the phase or the propagation time of the shear wave. The estimated phases or propagation time of the shear wave at the plurality of sampling locations are further used to derive the velocity value of the shear wave. The derived velocity value of the shear wave can be used to generate an ultrasound image, which process is known as radiation force impulse imaging, and/or to derive a mechanical property such as tissue viscosity or elasticity. Such conventional shear wave elastography techniques can provide tissue shear elasticity, shear viscosity and shear wave attenuation.

US2012/0089019A1 and US2011/0263978A1 are both directed to conventional shear wave elastography techniques, namely estimating tissue mechanical property on basis of its impact on the propagation of the shear wave.

SUMMARY OF THE INVENTION

Therefore, it would be advantageous to provide an improved ultrasound system and method for measuring a property (such as a tissue mechanical property) of a region of interest in a subject.

In accordance with an embodiment of a first aspect of the present invention, there is proposed an ultrasound imaging system. The ultrasound system comprises: an ultrasound probe configured to sequentially transmit, to each of a plurality of focal spots in the region of interest, a push pulse for generating a shear wave, each of the plurality of focal spots having a mutually different depth value, and to receive ultrasound echo signals adjacent to each of the plurality of focal spots; a shear wave detector configured to derive, for each of the plurality of focal spots, a first parameter indicating a property which the generated shear wave has at the focal spot, based on the received ultrasound echo signals; and a property estimator configured to estimate a second parameter indicating the property of the region of interest as a function of the derived first parameters.

In this way, a plurality of shear waves are excited at different depths in the region of interest and the property of the region of interest is estimated based on the intensities of the plurality of shear waves. The inventors of the present invention have recognized that the property of the region of interest impacts on the propagation of each push pulses as the push pulse propagates through the region of interest, and in turn impacts the respective shear wave excited by the push pulse at the focal spots in the region of interest, and thus the property (such as intensity, phase) of the excited shear waves at the focal spots will be dependent on the property (such as tissue viscosity, tissue stiffness, tissue attenuation) of the region of interest. For example, the tissue attenuates the propagation of the push pulse in such a way that the higher the tissue longitudinal attenuation factor, the more the push pulse attenuates as it propagates through the tissue, and thus the intensity of the push pulse at the focal spot and in turn the intensity of the excited shear wave becomes lower. Based on such recognition, the inventors of the present invention have proposed to excite a plurality of shear waves at different focal depths in the region of interest, and estimate the property of the region of interest as a function of properties of the share waves generated at the plurality of focal spots on basis of an impact of the property of the region of interest on the propagation of the push pulses along the longitudinal direction. In other words, the property of the region of interest is estimated based on the relationship between properties of the shear waves generated at the plurality of focal spots. For example, the first parameter derived for a focal spot can indicate a property (such as intensity, phase) which the generated shear wave has at the focal spot. To the contrary, in conventional shear wave elastography techniques, the property of the region of interest is estimated on basis of the impact of the property of the region of interest on the propagation of the shear wave along the traverse/lateral direction. Therefore, in conventional shear wave elastography techniques, the propagation property of the shear wave, such as propagation velocity or delay of the shear wave, is estimated, rather than any property, which the shear wave has at the focal spot before it even starts to propagate along the lateral direction, is estimated or derived.

Since the shear wave propagates in a direction perpendicular to the transmitting/receiving direction (i.e. the longitudinal direction) of the ultrasound signals, the measurement of the shear wave is not impacted by the backscatter of the ultrasound signals along the longitudinal direction. Thus, the above tissue property estimation does not have the aforementioned disadvantage of the conventional longitudinal wave-based tissue attenuation measurement.

In comparison to the conventional shear wave elastography techniques, additional properties of the region of interest can be estimated by combining the measured parameters of the plurality of shear waves. In some embodiments, the second parameter can indicate a longitudinal property of the region of interest, such as tissue longitudinal attenuation, tissue longitudinal viscosity, etc. As well-known, a tissue property may be the same in all directions, but may also be different in different direction. For example, a tissue mechanical property, such as tissue attenuation, tissue viscosity or tissue elasticity, in the longitudinal direction can be different from that in the traverse direction. A longitudinal property of the region of interest is known as the property of the region of interest along the longitudinal direction (i.e. the propagation of a longitudinal wave), such as longitudinal attenuation, longitudinal viscosity. Likewise, a traverse property, also called a shear property, is known as the property of the region of interest along the traverse direction, such as traverse attenuation (also called shear attenuation), traverse viscosity, etc.

The number of focal spots can be set to any suitable values. Generally, the larger the number of focal spots, the more accurate the estimated property of the region of interest becomes. The ultrasound probe can comprise a one-dimensional or two-dimensional transducer array. The region of interest can be a region of tissue, for example a region of liver tissue, kidney tissue, prostate tissue, breast tissue, etc. The subject can be a human such as a patient, an animal, a phantom etc. The property of the generated shear wave at the focal spot can be properties in time domain or frequency domain, including but not limited to the displacement, the velocity, and/or the spectrum of the shear wave.

In accordance with an embodiment, the property of the region of interest comprises any one of attenuation, stiffness, and viscosity of the region of interest. The property of the region of interest can comprise any one of tissue attenuation, tissue stiffness, and tissue viscosity. The tissue attenuation can be longitudinal attenuation or shear attenuation. The property of the region of interest can comprise a longitudinal property of the region of interest. For example, the property of the region of interest can be longitudinal attenuation.

By developing a special shear wave excitation and tracking scheme, we propose an integrated approach that enables estimation of additional parameters such as longitudinal wave attenuation. The proposed approach is envisioned as a one-button push tool that provides multi-parameter tissue quantification based on both longitudinal and shear waves. Clinical studies have long indicated that the acoustic attenuation coefficient of the longitudinal wave is useful for fat quantification in soft tissue (e.g. fatty liver quantification). Recently developed shear wave elastography has emerged as a diagnostic tool for tissue characterization (e.g. liver fibrosis staging) and cancer detection (e.g. cancer detection for liver, breast, prostate and thyroid etc.).

In accordance with an embodiment, the first parameter for a focal spot is derived from a displacement of the generated shear wave at a tracking spot adjacent to the focal spot. In other words, each first parameter is derived from a displacement which the generated shear wave exhibits at a tracking spot adjacent to a respective focal spot. Various known approaches can be used to derive the shear wave displacement from the echo signals, either in time domain or frequency domain. In various embodiments, the first parameter indicate a peak displacement, average displacement or the like of the generated shear wave at the tracking spot. Since the tracking spot is adjacent to the respective focal spot and the displacement at the tracking spot can be regarded as being proportional to the displacement at the focal spot, the derived first parameter can be used to indicate a displacement, such as a peak displacement, an average displacement or the like, of the generated shear wave at the respective focal spot.

In accordance with an embodiment, the first parameter is derived from a peak displacement of the generated shear wave at the tracking spot to indicate the peak displacement of the generated shear wave at the focal spot.

In accordance with an embodiment, the property estimator is configured to estimate a tissue longitudinal attenuation property of the region of interest by means of fitting an exponential curve with the derived first parameters.

In accordance with an embodiment, the ultrasound system further comprises an interface, wherein the interface is configured to receive an input for indicating the plurality of focal spots; and the property estimator is further configured to estimate the second parameter based on the focal depth value of each of the indicated plurality of focal spots. In an example, the user input can be the region of interest, and then the plurality of focal spots can be automatically set in accordance with a predetermined rule. For example, the plurality of focal spots can be set as a predetermined number of spots equally spaced across the region of interest. In another example, the input can be the plurality of focal spots. The interface can be a user interface or an interface with a system capable of delivering the required information, such as a hospital information system, patient information management system.

In accordance with an embodiment, the ultrasound system further comprises an intensity variation estimator configured to estimate, for each of the plurality of focal spots, an intensity variation of the push pulse caused by beamforming setting of the push pulse.

The inventors of the present invention recognize that the estimation of certain properties of the region of interest may utilize the initial acoustic intensity of the push pulse, but the initial acoustic intensity of the push pulse varies with the beam profile of the push pulse. In order to further improve the estimation regarding a property of the region of interest, the inventors of the present invention propose to estimate such variation and compensate for such variation.

In some embodiments, the ultrasound probe is further configured to adjust the intensity of the push pulse based on the estimated variation. In some other embodiments, the property estimator is further configured to estimate the second parameter based on the estimated variation.

In accordance with an embodiment, the shear wave detector is further configured, for each of the plurality of focal spots, to estimate a third parameter indicating a tissue shear property of the region of interest at the depth of the focal spot, and to adjust the first parameter based on the estimated third parameter, and the property estimator is further configured to derive the second parameter as a function of the adjusted first parameters. For example, the shear property of the region of interest can be shear stiffness, shear viscosity, or shear attenuation of the region of interest. For example, the shear property at the depth of each focal spot can be estimated based on the velocity of the respective shear wave generated at that focal spot.

The inventors of the present invention recognize that the local shear properties at different depths may be different, and thus impact the estimation of the property of the region of interest, and therefore, they propose to adjust the first parameters with the local shear wave properties prior to the estimation of the property of the region of interest.

In accordance with an embodiment, the ultrasound probe is configured, for each of the plurality of focal spots, to transmit a tracking pulse toward a tracking spot adjacent to the focal spot, to receive an ultrasound echo signal from the tracking spot; and the shear wave detector is configured to derive, for each of the plurality of focal spots, the first parameter, based on the ultrasound echo signal received from a tracking spot adjacent to the focal spot.

In accordance with an embodiment of a second aspect of the present invention, there is proposed a method of measuring a property of a region of interest in a subject by using shear wave. The method comprises: sequentially transmitting, to each of a plurality of focal spots in the region of interest, a push pulse for generating a shear wave, each of the plurality of focal spots having a mutually different depth value, and for receiving ultrasound echo signals adjacent to each of the plurality of focal spots; deriving, for each of the plurality of focal spots, a first parameter indicating a property which the generated shear wave has at the focal spot, based on the received ultrasound echo signals; and estimating a second parameter indicating the property of the region of interest as a function of the derived first parameters.

In accordance with an embodiment of a third aspect of the present invention, there is provided a computer product, comprising computer program instructions which, when executed, perform the method of estimating a property of a region of interest in a subject based on a plurality of shear waves, each of the plurality shear waves being generated by transmitting a push pulse to a focal spot at a different depth, wherein the method comprises: deriving, for each of a plurality of focal spots, a first parameter indicating a property which the shear wave has at the focal spot, based on ultrasound echo signals received adjacent to each of the plurality of focal spots; and estimating a second parameter indicating the property of the region of interest as a function of the derived first parameters.

Other objects and advantages of the present invention will become more apparent and can be easily understood with reference to the description made in combination with the accompanying drawings.

DESCRIPTION OF THE DRAWINGS

The present invention will be described and explained hereinafter in more detail in combination with embodiments and with reference to the drawings, wherein.

The same reference signs in the figures indicate similar or corresponding features and/or functionalities.

DETAILED DESCRIPTION

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

Figure 2:
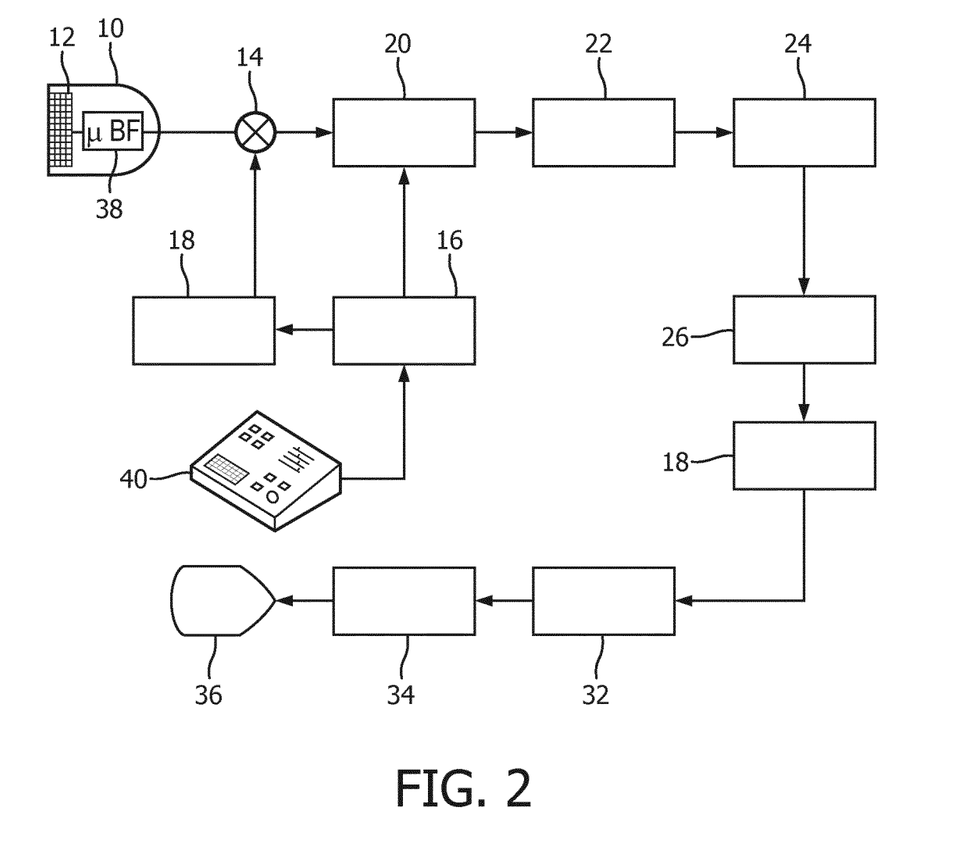
FIG. 2 illustrates in a block diagram form an ultrasound imaging system constructed in accordance with some embodiments of the present invention.

Referring first to FIG. 2, an ultrasound system constructed in accordance with some embodiments of the present invention is shown in block diagram form.

An ultrasound probe 10 has a one-dimensional or two-dimensional array 12 of transducer elements for transmitting and receiving ultrasound signals. The transducer array 12 can scan a two dimensional (2D) plane by transmitting beams and receiving returning echo signals over a single plane in the body, and can also be used to scan a volumetric region by transmitting beams in different directions and/or planes of a volumetric (3D) region of the body. The array elements are coupled to a micro-beamformer 38 located in the probe which controls transmission by the elements and processes the echo signals received from groups or sub-arrays of elements into partially beam-formed signals. The partially beam-formed signals are coupled from the probe to a multiline receive beamformer 20 in the ultrasound system by a transmit/receive (T/R) switch 14. Coordination of transmission and reception by the beamformers is controlled by a beamformer controller 16 coupled to the multiline receive beamformer and to a transmit controller 18, which provides control signals to the micro-beamformer. The beamformer controller is responsive to signals produced in response to user manipulation of a user control panel 40 to control the operation of the ultrasound system and its probe. The multiline receive beamformer 20 produces one or more, spatially distinct, tracking lines (also known as receive lines or A-lines) of echo signals during a single transmit-receive interval.

In accordance with an embodiment of the present invention, the ultrasound probe is configured to sequentially transmit, to each of a plurality of focal spots in the region of interest, a push pulse for generating a shear wave, each of the plurality of focal spots having a mutually different focal depth value, and to receive ultrasound echo signals adjacent to each of the plurality of focal spots. For example, the ultrasound echo signals are received along an A-line adjacent to each focal spot.

The received echo signals are then coupled to a shear wave detector for further processing. The shear wave detector is configured to derive, for each of the plurality of focal spots, a first parameter of a property of the respective shear wave, based on the received ultrasound echo signals. The shear wave detector comprises a signal processor 22, an A-line memory 24, an A-line motion estimator (e.g. cross-correlator) 26, and an intensity detector 28. The echo signals are processed by filtering, noise reduction, and the like, by a signal processor 22, and are then stored in an A-line memory 24. The echo signals of successive A-line samplings are tracked by an A-line motion estimator 26 to produce a time sequence of samples of tissue displacement for each sampling location. The intensity detector 28 is responsive to detection of the shear wave displacement along the A-lines to determine the intensity of the shear wave. A property estimator 32 is coupled to estimate a second parameter indicating the property of the region of interest, based on a function of the derived first parameters. The shear wave detector and the property estimator 32 will be described in more detail below by referring to FIG. 3.

In some embodiments, the derived property information can be coupled to an image processor 34 which processes the property information, preferably in combination with the anatomical ultrasound image of the tissue, for display on an image display 36.

In some embodiments, the ultrasound system can further comprise an intensity variation estimator 40 configured to estimate, for each push pulse, a variation of an initial acoustic intensity of the push pulse caused by a beam profile of the push pulse. In an example, the ultrasound probe 10 is further configured to adjust the intensity of the push pulse based on the estimated variation. In this case, the intensity variation estimator 40 may be part of the beamformer controller 16. In another example, the property estimator 32 is configured to estimate the second parameter further, based on the estimated variation. Such intensity variation caused by a beam profile and the corresponding compensation will be described in more detail below by referring to FIG. 5.

Figure 3:
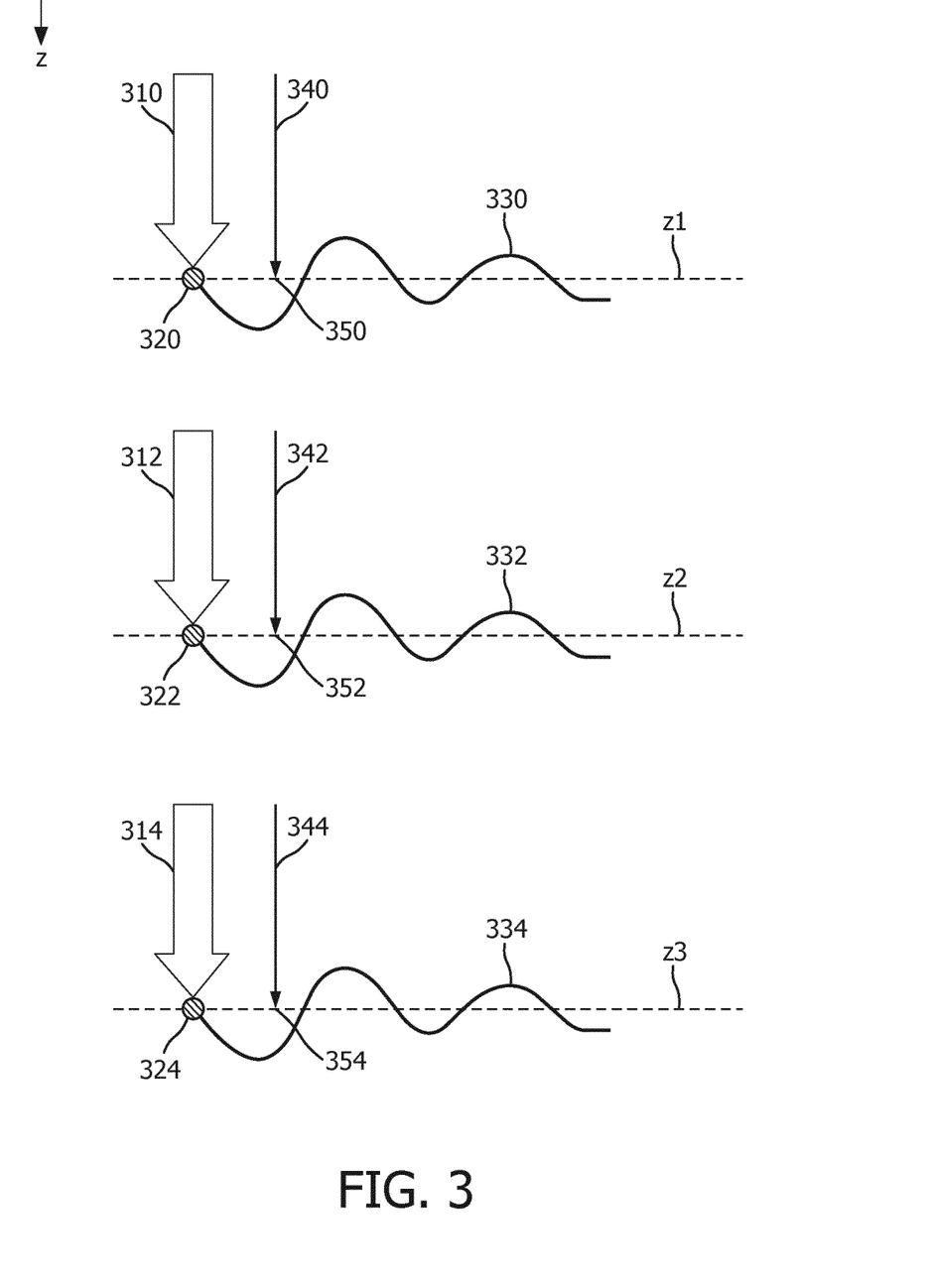
FIG. 3 illustrates a plurality of shear waves generated at a plurality of focal spots in the region of interest in accordance with some embodiments of the present invention.

FIG. 3 illustrates a plurality of shear waves generated at the plurality of focal spots in the region of interest in accordance with an embodiment of the present invention. Although three shear waves are illustrated in FIG. 3, a different number of shear waves may be generated in accordance with various embodiments.

Referring to FIG. 3, each of a plurality of push pulses 310, 312, 314 is focused at a different depth z1, z2, z3 under the skin surface. The tissue deformation caused at each focal spot 320, 322, 324 results in a shear wave 330, 332, 334 propagating along a lateral direction (such as direction x as illustrated) orthogonal to the longitudinal direction z.

The push pulse can be a focused high MI push pulse (e.g., MI of 1.9 or less so as to be within FDA diagnostic limits) which displaces the tissue at the focal spot downward and causes the development of a shear wave. Typically, ultrasound signals, e.g. the push pulse, travels at a speed of about 1560 meters/sec in tissue, shear waves travel at a speed of about 1-5 meters/sec in tissue, and a shear wave period in tissue is of the order of 2 to 10 milliseconds. In some embodiments, the plurality of push pulses can be sequentially transmitted at a predetermined time interval. For example, the predetermined time interval can be greater than at least one period of the shear wave.

Figure 4:
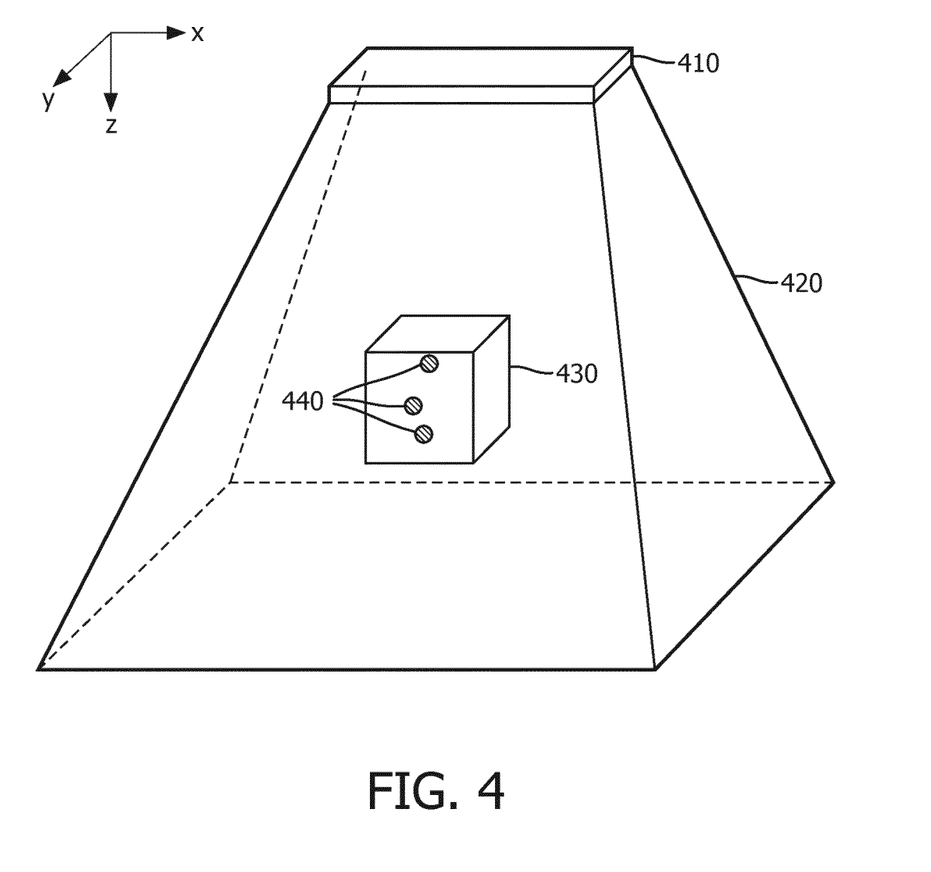
FIG. 4 illustrates the plurality of focal spots in the region of interest in accordance with some embodiments of the present invention.

FIG. 4 illustrates a plurality of focal spots in the region of interest in accordance with some embodiments of the present invention. In FIG. 4, direction z represents the longitudinal direction of the ultrasound probe 410, namely the propagation direction of ultrasound signals, also known as depth direction; directions x and y respectively represent the directions perpendicular to the longitudinal direction, namely the azimuth direction and elevation azimuth direction of the ultrasound probe 410. Although an ultrasound probe 410 comprising a two-dimensional transducer array has a three-dimensional field of view 420 is illustrated, it will be appreciated that an ultrasound probe having a one-dimensional transducer array can be used as well, and the region of interest can be two-dimensional or three-dimensional.

Referring to FIG. 4, a plurality of spatial locations 440 inside the region of interest 430 are used as focal spots. Three focal spots are illustrated, but the present invention is not limited thereto and any number of focal spots may be defined. The focal spots 440 are located at different depths and, in other words, at different positions along the longitudinal direction z. In an embodiment, the plurality of focal spots can be spaced the same predetermined distance apart from each other along the longitudinal direction. The predetermined distance can be, for example, of the order of one centimeter. The plurality of focal spots 440 may have the same or a different position along the other two directions x and y in various embodiments.

The plurality of focal spots can be manually selected via a user interface. For example, an ultrasound image containing the region of interest is presented on a display, and then the user can select the focal spots by entering the corresponding spatial locations in the displayed ultrasound image via any suitable user input means, including but not limited to joy stick, mouse, physical buttons, touch screen, etc. Additionally or alternatively, the focal spots can be automatically generated in the region of interest. For example, a predetermined number of focal spots may be generated, and/or a plurality of focal spots, spaced the same predetermined distance apart, may be generated. The predetermined number and/or the predetermined distance can be selected by the user or can be pre-defined.

The region of interest can also be manually selected via a user interface in a displayed ultrasound image, and/or can be automatically or semi-automatically defined by means of, for example, processing an ultrasound image.

Referring back to FIG. 3, ultrasound echo signals are received along the tracking lines 340, 342, 344 adjacent to the focal spots to track the tissue displacement at the tracking spot 350, 352, 354. The inventors of the present invention have recognized that the shear wave tracking at the focal spot is not so accurate due to the push pulse reflection or reverberation, for example at a tracking spot adjacent to the focal spot, and thus they propose to track the shear wave displacement at tracking spots adjacent to the focal spot. Further, the tracking spots shall not be located too far away from the focal spot, because the shear wave displacement decreases quickly along the propagation direction. The distance between each focal spot and the nearest tracking spot can be any suitable value and can be different for different kinds of region of interest. For example, the distance between the tracking spot and the focal spot can be of the order of 0.1 cm. For example, the distance between the tracking spot and the focal spot can be set at half the push beam width away from the push focus For each of the plurality of focal spots, a first parameter indicating a property of the shear wave is derived from the echo signals received along the respective tracking line. Taking focal spot 320 as an example, the first parameter derived for the focal spot 320 is derived from the echo signal received along the tracking line 340. In some embodiments, the first parameter derived for a focal spot may indicate a property value of the respective shear wave at that focal spot. In accordance with an embodiment of the present invention, the first parameter is derived as the peak value of the shear wave displacement at the tracking spot 350, 352, 354. In other examples, the first parameter may be derived as an average displacement or the like of the shear wave.

Next, a property of the region of interest is estimated as a function of the shear wave property values at the plurality of focal spots. In some embodiments, the shear wave property value at each focal spot is modeled as a function of the intensity of the push pulse, the property of the region of interest, and the depth value of the focal spot, and then the unknown property of the region of interest may be derived in accordance with such a model. Note that the unknown property to be derived is assumed to be the same within the region of interest. Taking the tissue attenuation as an example, the estimation in accordance with an embodiment is described below.

In accordance with an embodiment of the present invention, the peak or maximum displacement $M_k$ of the k-th shear wave measured at the respective tracking spot can be modeled as being proportional to the intensity $I_k$ of the push pulse multiplied by an exponential form whose exponent is a negative tissue attenuation coefficient $\alpha$ multiplying the depth $d_k$ of the respective focal spot, namely, $$M_k = f(I_k, \alpha, d_k) = A \cdot I_k \cdot e^{-\alpha d_k}.$$

For example, the estimated tissue attenuation coefficient $\alpha$ can be mathematically derived as:

$$\hat{\alpha} = \underset{\alpha}{\operatorname{argmin}} \|M_k - f(I_k, \alpha, d_k)\|^2$$

For example, the estimation of the tissue attenuation coefficient can be performed by means of fitting an exponential curve with the derived first parameters $M_k$. In some embodiments, the intensity $I_k$ of the push pulses 310, 312, 314 can be set as being substantially the same. In some other embodiments, the intensity of the push pulses 310, 312, 314 can be set to be different.

The inventors of the present invention have recognized that the estimation of certain properties of the region of interest may utilize the initial acoustic intensity of the push pulse, but the initial acoustic intensity of the push pulse varies with the beam profile of the push pulse. For example, the inventors have theoretically derived that the peak or maximum shear wave displacement $M_d$ at the focal spot having depth value d is proportional to the initial acoustic intensity $I_0$ of the push pulse multiplied by an exponential form whose exponent is a negative tissue attenuation coefficient $\alpha$ multiplying the depth d, namely $$M_d \propto I_0 \cdot e^{-\alpha \cdot d}.$$

In order to further improve the estimation about the property of the region of interest, the inventors of the present invention propose to estimate such variation and compensate such variation.

Figure 5:
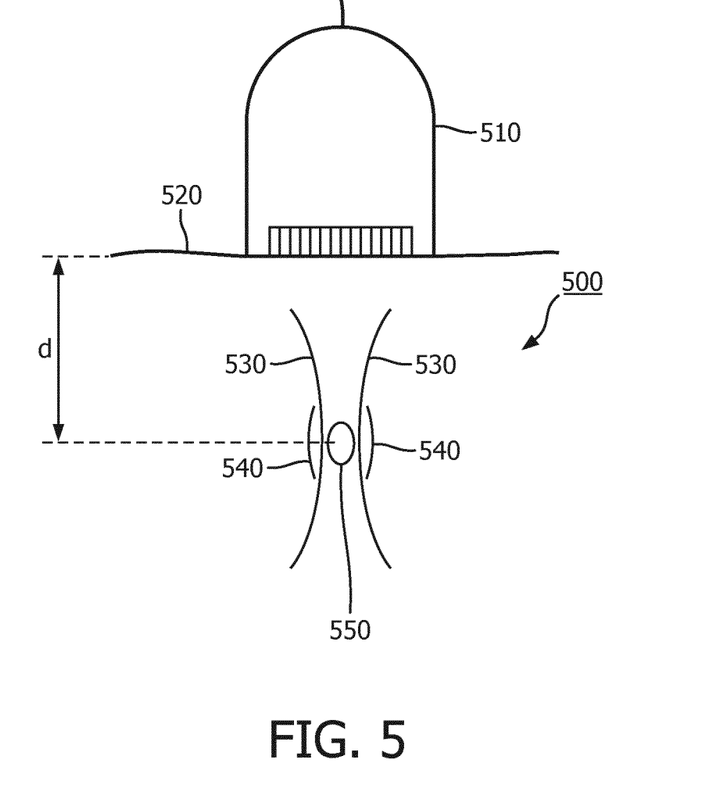
FIG. 5 illustrates a beam profile of a push pulse focused at a focal depth in accordance with an embodiment of the present invention.

FIG. 5 illustrates a beam profile of a push pulse focused at a focal depth in accordance with an embodiment of the present invention. Referring to FIG. 5, the ultrasound probe 510 at the skin surface 520 transmits a push pulse with a beam profile 530 through the body 500 to a given focal spot in the region of interest. The focal spot is indicated by the shaded area 550 having a focal depth value d. This push pulse will displace the tissue at the focus in a downward direction, resulting in a shear wave front 540 emanating outward from the displaced tissue. For generating a certain beam profile, different transducer elements may be used, and different energy weights, phase shifts may be applied to the used transducer elements. This results in that the initial acoustic intensity $I_0$ of the push pulse can be different even if the intensity of the push pulse is set to be the same. The variation of the initial acoustic intensity can be determined for a given beam profile.

In accordance with an embodiment of the present invention, an intensity estimator is configured to estimate such intensity variation. For example, when being provided by a beam profile, the intensity estimator can be configured to estimate the intensity variation of this beam profile by online calculation on the basis of a predetermined modeling, or by retrieving the intensity variation from a pre-stored look-up table.

In accordance with an embodiment of the present invention, the ultrasound probe is further configured to adjust the intensity of the push pulse based on the estimated intensity variation. For example, in order to achieve a predetermined initial acoustic intensity value, the intensity of a push pulse with a beam profile is determined on the basis of the predetermined initial acoustic intensity value and the estimated intensity variation caused by the beam profile, and then the ultrasound probe transmits the push pulse with the determined intensity. Alternatively, the property estimator is further configured to estimate the second parameter based on the estimated variation. For example, for a push pulse with a beam profile, the compensated initial acoustic intensity value can be determined on the basis of the intensity of the push pulse and the estimated intensity variation caused by the beam profile and then the property estimator uses the compensated initial acoustic intensity value to estimate the property of the region of interest.

In accordance with an embodiment, the shear wave detector is further configured, for each of the plurality of focal spots, to estimate a third parameter indicating a shear property of the region of interest at the depth of the focal spot, and to adjust the first parameter based on the estimated third parameter; and the property estimator is further configured to derive the second parameter as a function of the adjusted first parameters.

For example, the shear property of the region of interest can be shear stiffness or viscosity of the region of interest. For example, the shear property at the depth of each focal spot can be estimated based on the velocity of the respective shear wave generated at that focal spot.

The shear property of the region of interest at the depth of a focal spot can be estimated by means of conventional shear wave elastography techniques or any other suitable means developed in the future. In the case of using the conventional shear wave elastography techniques, for each of the generated shear waves, more than one tracking spots are spaced along the traverse direction x away from the respective focal spot, the ultrasound echo signals are received along the more than one tracking spots, the velocity of the respective shear wave is derived from the received ultrasound echo signals, and then the shear property such as tissue shear stiffness and viscosity is estimated from the derived velocity of the respective shear wave.

The technique processes described herein may be implemented by various means. For example, these techniques may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. In the case of software, implementation can be through modules (e.g., procedures, functions, and so on) that perform the functions described herein. The software codes may be stored in a memory unit and executed by the processors.

Moreover, aspects of the claimed subject matter may be implemented as a method, apparatus, system, or article of manufacture, using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Of course, those skilled in the art will recognize that many modifications may be made to this configuration without departing from the scope or spirit of what is described herein.

As used in this application, the terms "beamformer", "controller", "processor", "cross-correlator", "detector", "estimator" such as "shear wave detector", "property estimator" and "imaging encoder" are intended to refer to a processor or a computer-related entity, either hardware, a combination of hardware and software, software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed among two or more computers.

What has been described above includes examples of one or more embodiments. It is, of course, not possible to describe every conceivable combination of components or methodologies for the purpose of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. An ultrasound system for measuring a property of a region of interest in a subject by using shear wave, comprising:
an ultrasound probe configured to sequentially transmit, to each of a plurality of focal spots in the region of interest, a push pulse for generating a shear wave, each of the plurality of focal spots having a mutually different depth value, and to receive ultrasound echo signals adjacent to each of the plurality of focal spots;
a shear wave detector configured to derive, for each of the plurality of focal spots, a first parameter indicating a property which the generated shear wave has at the focal spot based on the received ultrasound echo signals; and
a property estimator configured to estimate a second parameter indicating the property of the region of interest as a function of the derived first parameters at the plurality of focal spots, wherein the property of the region of interest comprises a longitudinal property of the region of interest, the longitudinal property of the region of interest being a property of the region of interest along the propagation direction of the push pulses.

2. The ultrasound system of claim 1, wherein the first parameter derived for a focal spot indicates an intensity which the generated shear wave has at the focal spot.

3. The ultrasound system of claim 1, wherein the first parameter for a focal spot is derived from a displacement of the generated shear wave at a tracking spot adjacent to the focal spot.

4. The ultrasound system of claim 3, wherein the first parameter is derived from a peak displacement of the generated shear wave at the tracking spot.

5. The ultrasound system of claim 4, wherein the property estimator is configured to estimate a tissue longitudinal attenuation property of the region of interest by means of fitting an exponential curve with the derived first parameters.

6. The ultrasound system of claim 1, further comprising an interface, wherein
the interface is configured to receive an input for indicating the plurality of focal spots; and
the property estimator is further configured to estimate the second parameter based on the focal depth value of each of the indicated plurality of focal spots.

7. The ultrasound system of claim 1, wherein the property estimator is configured to estimate the second parameter as a second function of the derived first parameters and an intensity of the push pulses.

8. The ultrasound system of claim 1, further comprising an intensity variation estimator configured to estimate, for each push pulse, a variation of an initial acoustic intensity of the push pulse caused by a beam profile of the push pulse.

9. The ultrasound system of claim 8, wherein the ultrasound probe is further configured to adjust, for each push pulse, the intensity of the push pulse based on the estimated variation.

10. The ultrasound system of claim 8, wherein the property estimator is further configured to estimate the second parameter based on the estimated variations.

11. The ultrasound system of claim 1, wherein
the shear wave detector is further configured, for each of the plurality of focal spots, to estimate a third parameter indicating a shear property of the region of interest at the depth of the focal spot, and to adjust the first parameter based on the estimated third parameter; and
the property estimator is further configured to derive the second parameter as a function of the adjusted first parameters at the plurality of focal spots.

12. A method of measuring a property of a region of interest in a subject by using shear wave, comprising:

sequentially transmitting with an ultrasound probe, to each of a plurality of focal spots in the region of interest, a push pulse for generating a shear wave, each of the plurality of focal spots having a mutually different depth value, and receiving ultrasound echo signals adjacent to each of the plurality of focal spots;

deriving, for each of the plurality of focal spots, a first parameter indicating a property which the generated shear wave has at the focal spot, based on the received ultrasound echo signals; and estimating a second parameter indicating the property of the region of interest as a function of the derived first parameters at the plurality of focal spots, wherein the property of the region of interest is a longitudinal property of the region of interest, the longitudinal property of the region of interest being a property of the region of interest along the propagation direction of the push pulses.

13. A computer product, comprising computer program instructions stored on a non-transitory medium which, when being executed, perform a method of estimating a property of a region of interest in a subject based on a plurality of shear waves, each of the plurality of shear waves being generated by transmitting, with an ultrasound probe, a push pulse to a focal spot at a different depth, the method comprising:

deriving, for each of a plurality of focal spots, a first parameter indicating a property which the shear wave has at the focal spot, based on ultrasound echo signals received adjacent to each of the plurality of focal spots; and estimating a second parameter indicating the property of the region of interest as a function of the derived first parameters at the plurality of focal spots, wherein the property of the region of interest is a longitudinal property of the region of interest, the longitudinal property of the region of interest being a property of the region of interest along the propagation direction of the push pulses.

14. The method of claim 12, further comprising displaying the second parameter on an image display.

15. The computer product of claim 13, wherein the method further comprises providing the second parameter of interest to an image processor for display on an image display.

* * * * *